United States Patent [19]

von Bebenburg, deceased et al.

[11] Patent Number: 4,481,205

[45] Date of Patent: Nov. 6, 1984

[54] 2-AMINO-3-CARBETHOXYAMINO-6-(P-FLUORO-BENZYLAMINO)-PYRIDINE-MALEATE

[75] Inventors: Walter von Bebenburg, deceased, late of Dreieich, Fed. Rep. of Germany, by Marie von Bebenburg, administratrix; Siegfried Pauluhn, Frankfurt am Main, Fed. Rep. of Germany

[73] Assignee: Degussa Aktiengesellschaft, Frankfurt am Main, Fed. Rep. of Germany

[21] Appl. No.: 298,886

[22] Filed: Sep. 2, 1981

[30] Foreign Application Priority Data

Sep. 13, 1980 [DE] Fed. Rep. of Germany ....... 3034638

[51] Int. Cl.$^3$ .................... C07D 213/75; A61K 31/44
[52] U.S. Cl. .................................... 424/263; 546/307; 546/308
[58] Field of Search ............... 546/308, 304, 305, 306; 424/263

[56] References Cited

U.S. PATENT DOCUMENTS 3,969,361  7/1976  von Bebenburg et al. ......... 546/308

FOREIGN PATENT DOCUMENTS 1795858  1/1979  Fed. Rep. of Germany ...... 546/308

*Primary Examiner*—Alan L. Rotman
*Attorney, Agent, or Firm*—Cushman, Darby & Cushman

[57] ABSTRACT

There is prepared 2-amino-3-carbethoxyamino-6-(p-fluoro-benzylamino)-pyridine-maleate of the formula

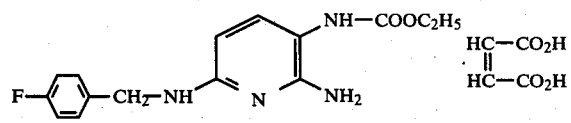

The compound has antiphlogistic and analgesic properties in the same manner as the known hydrochloride salt. In contrast to the hydrochloride 2-amino-3-carbethoxyamino-6-(p-fluoro-benzylamino)-pyridine-maleate can be produced without a disturbing blue coloration. This maleate generally is formed from a mixture of two crystal modifications A and B, whereby there is especial advantageous in regard to isolation as well as the galenical preparations a mixture enriched in modification A (60 to 90% modification A).

22 Claims, 20 Drawing Figures

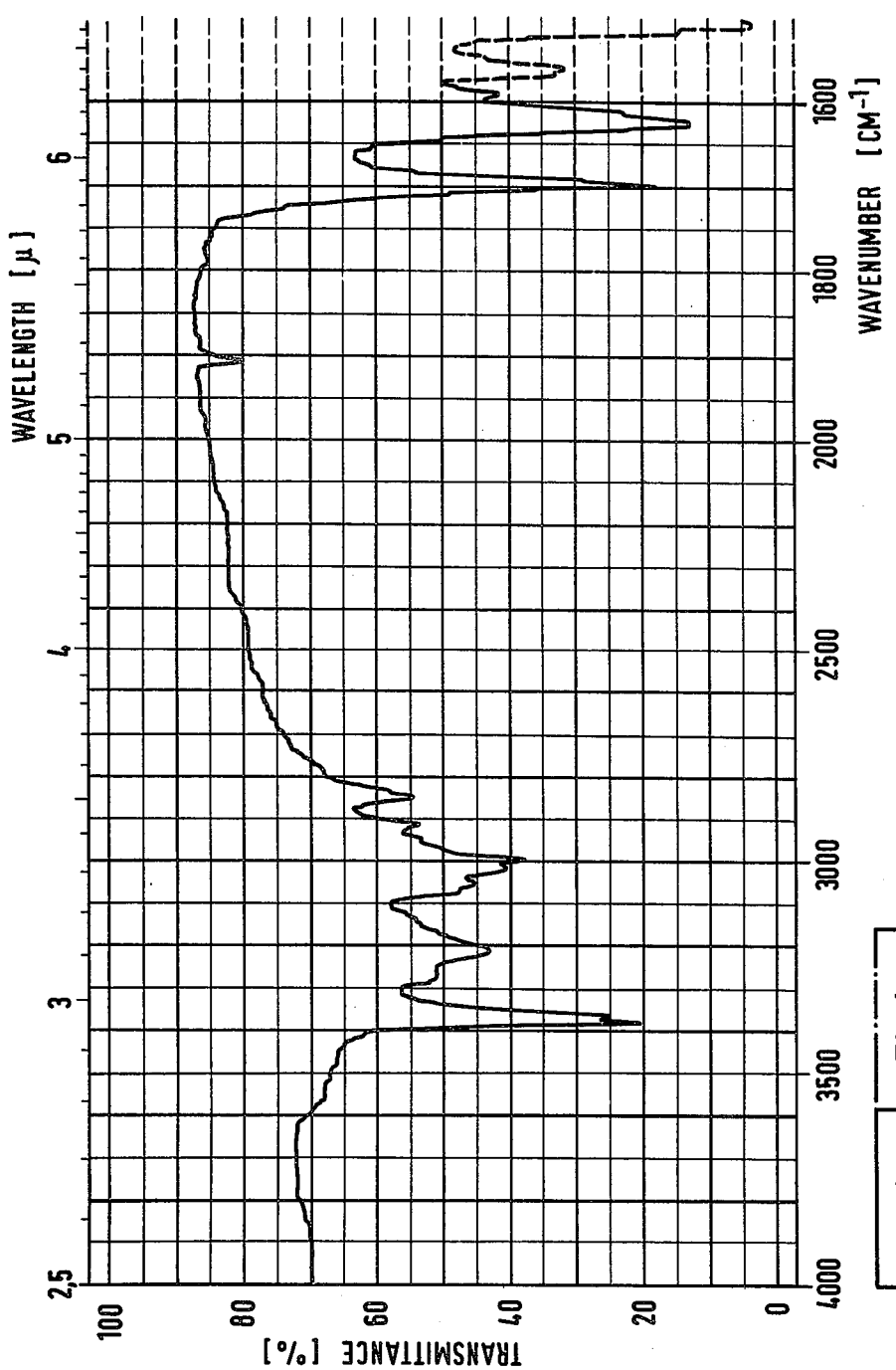

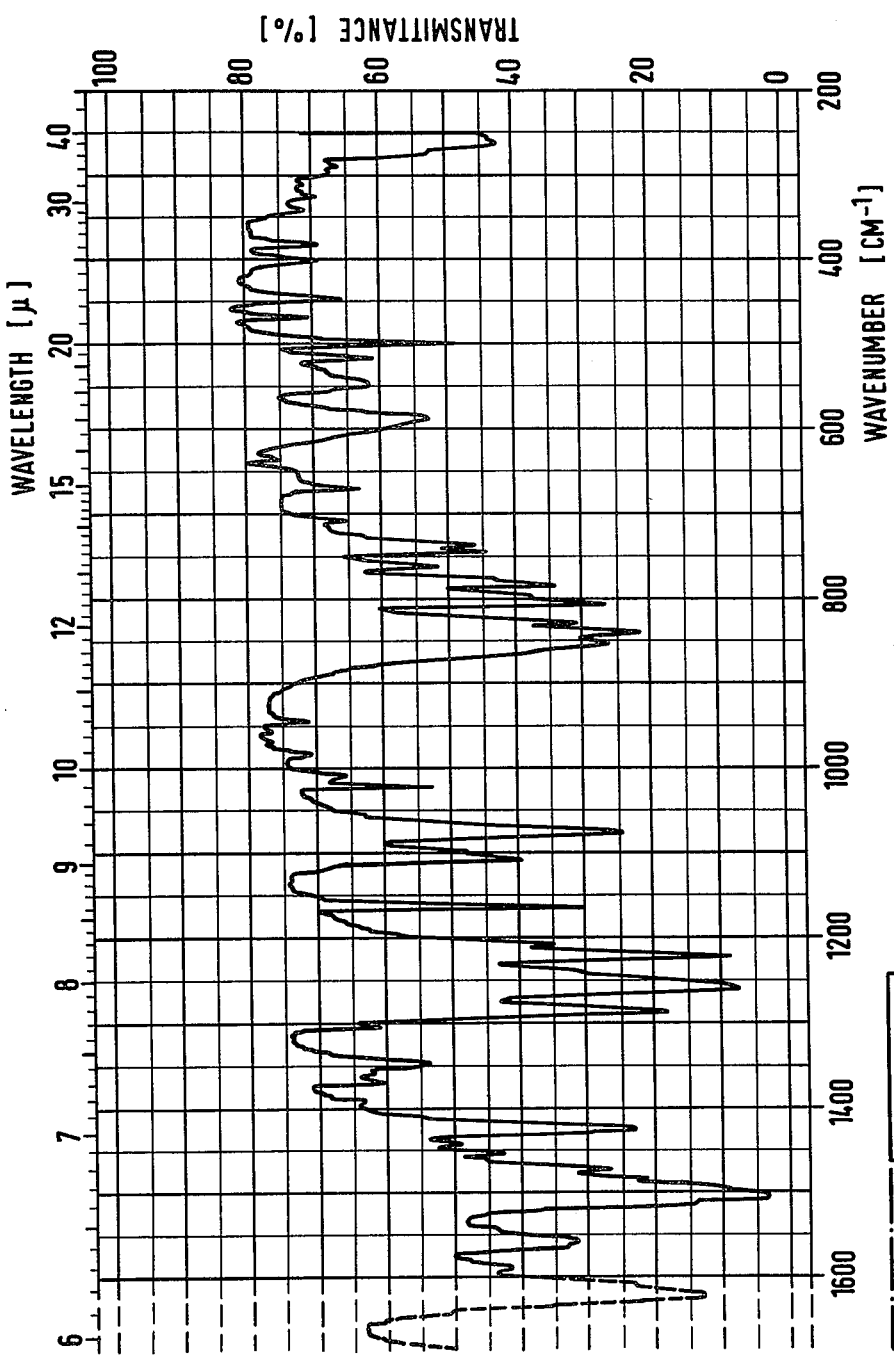

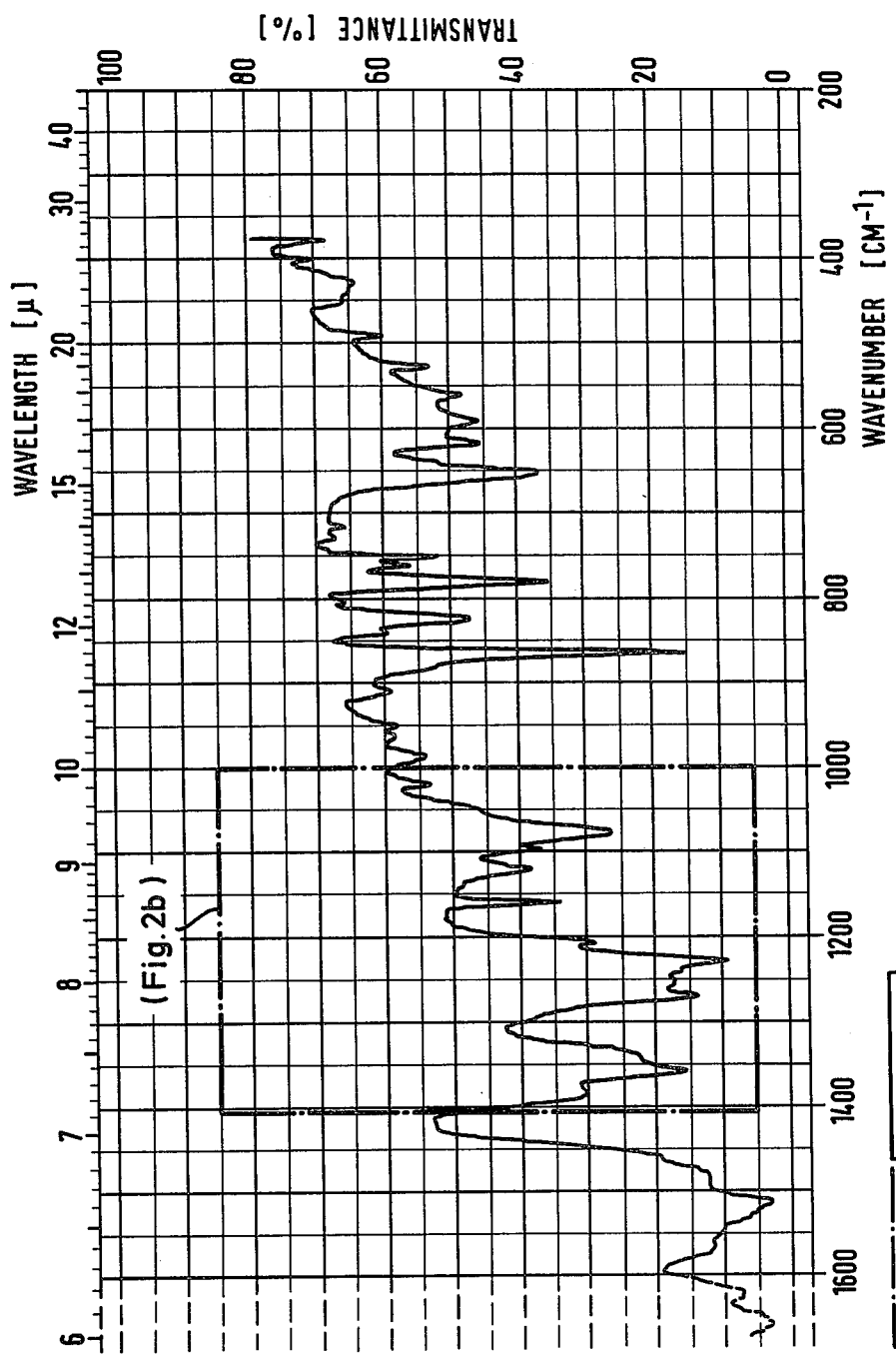
*Fig. 2a (II)*

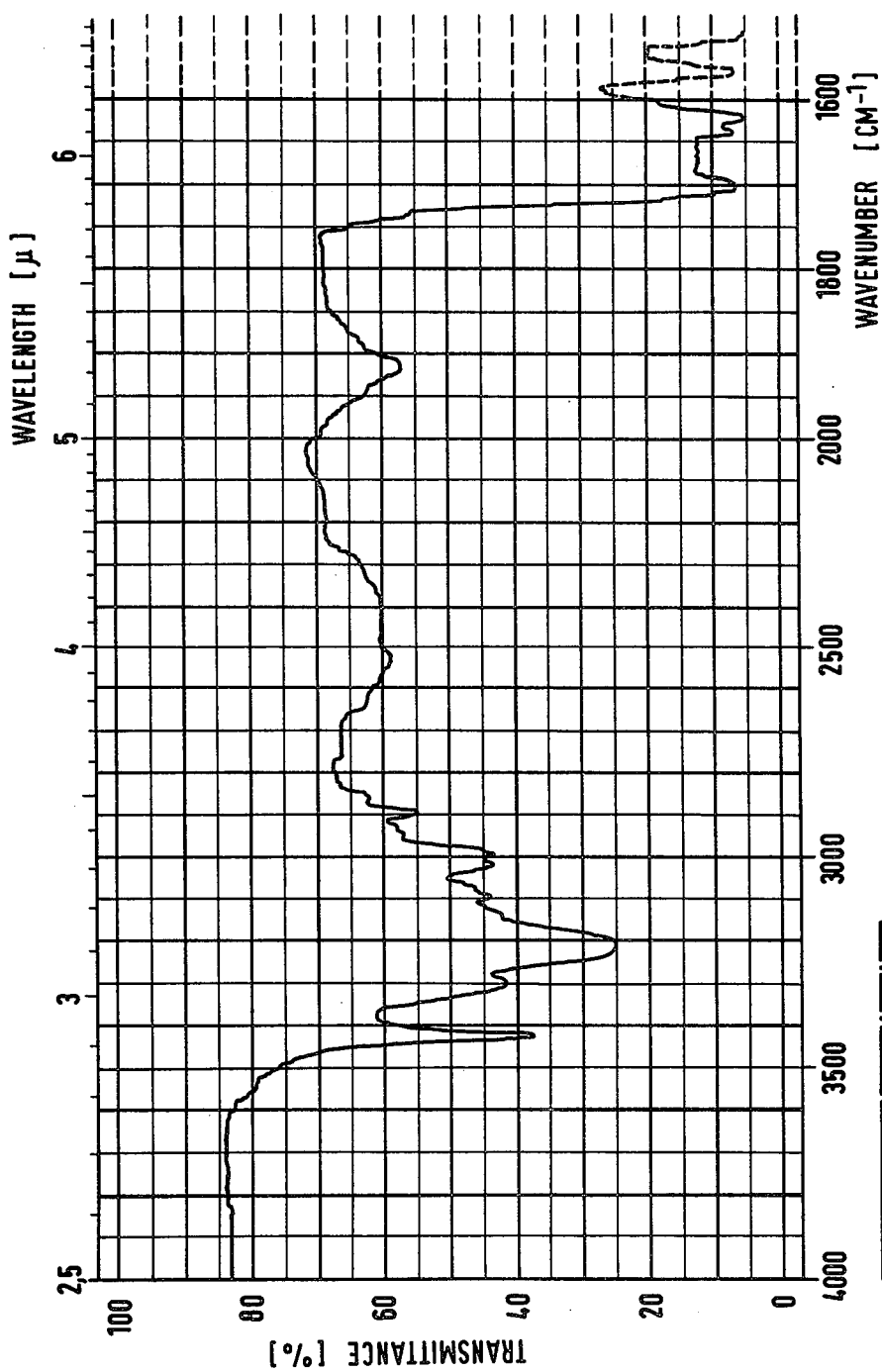

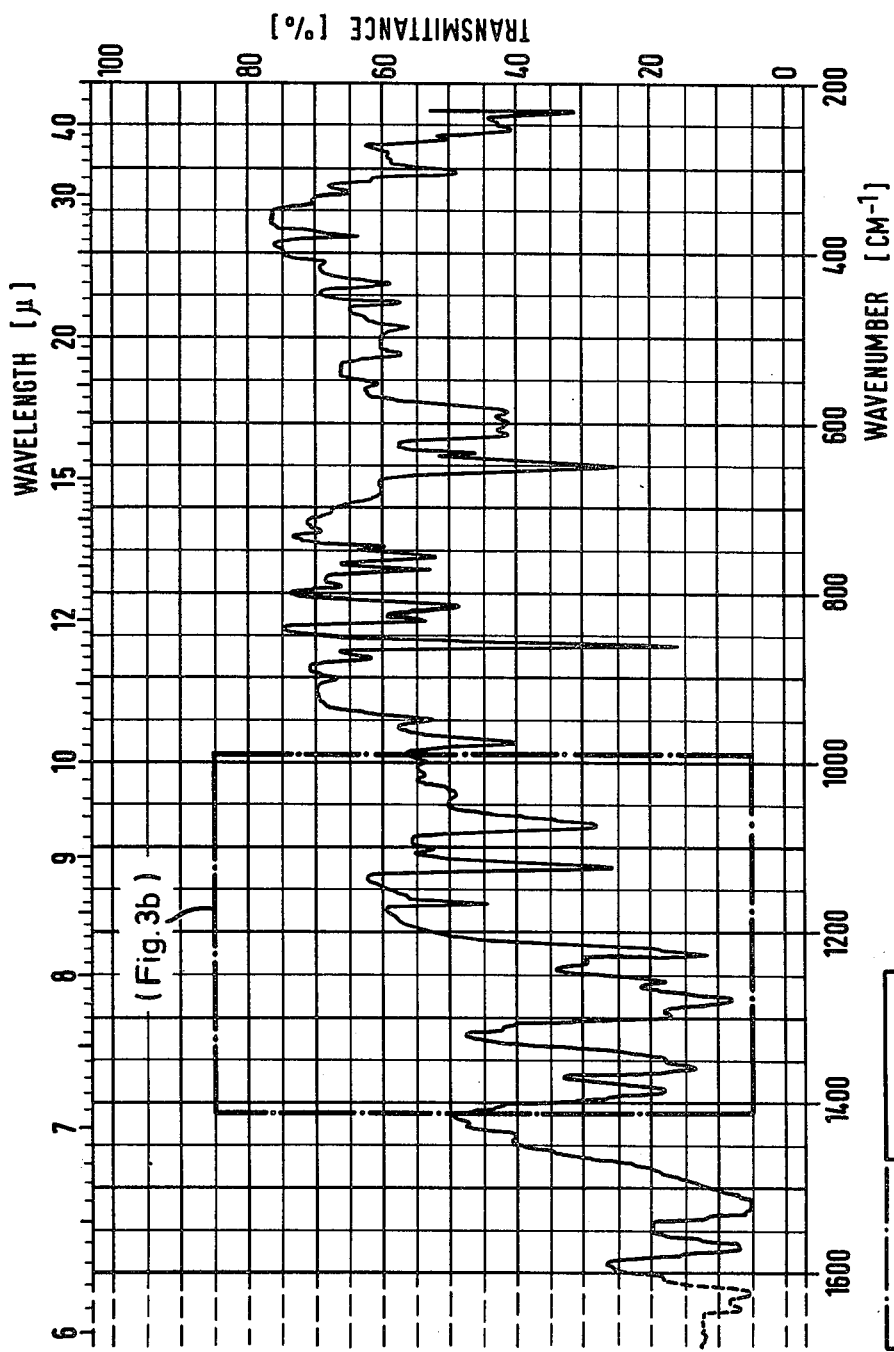
Fig. 3a (II)

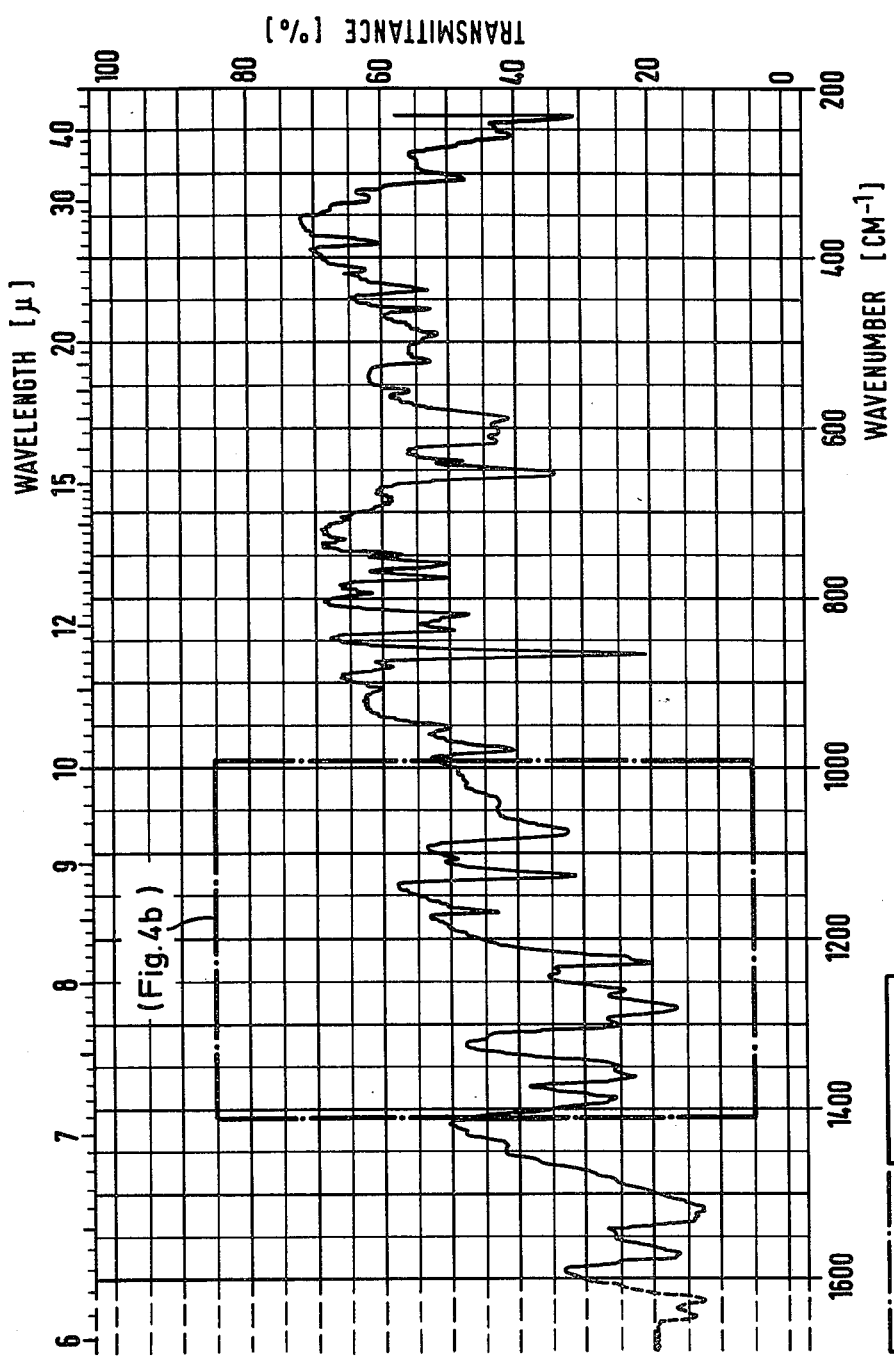
Fig. 4a (II)

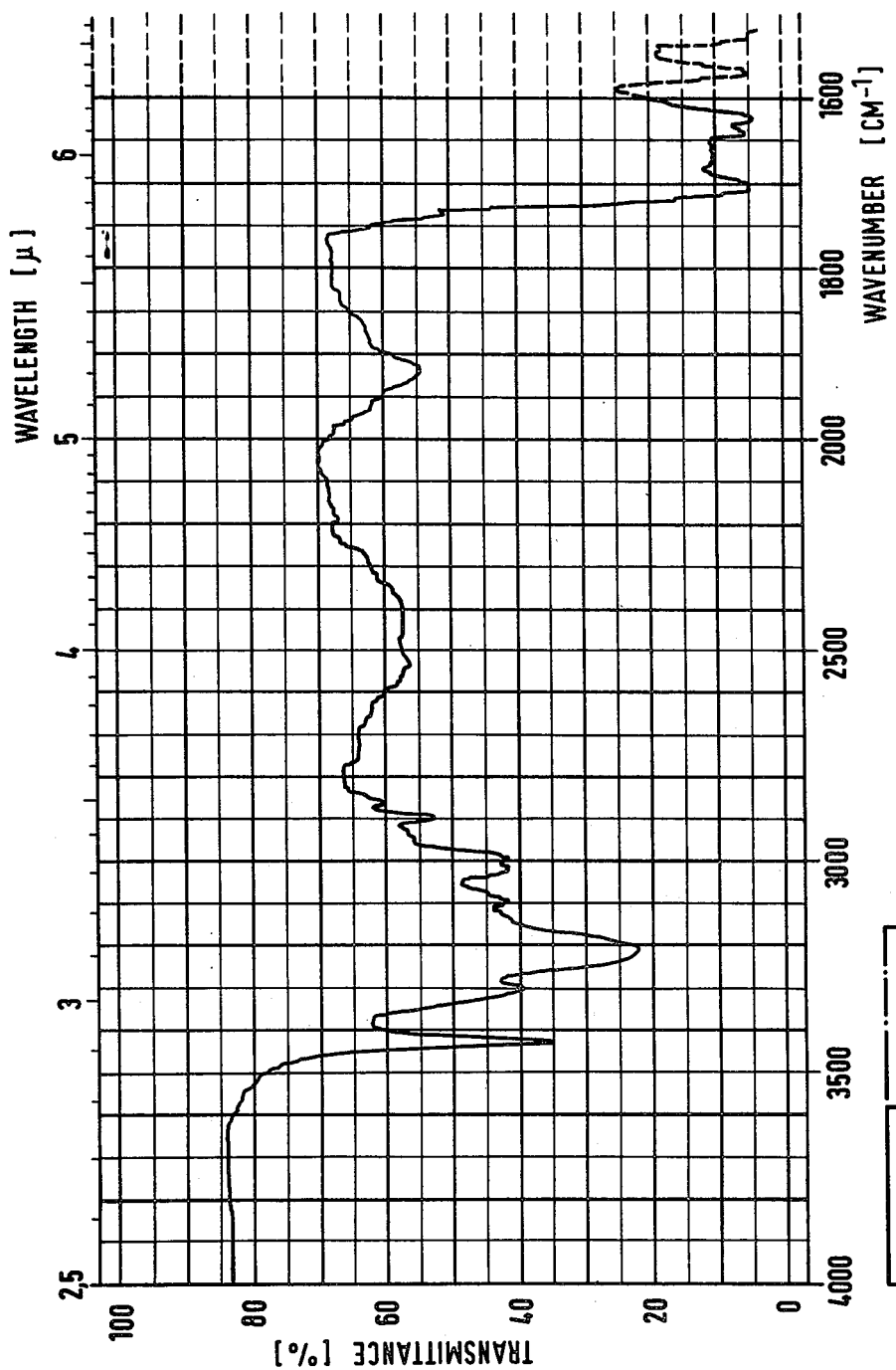

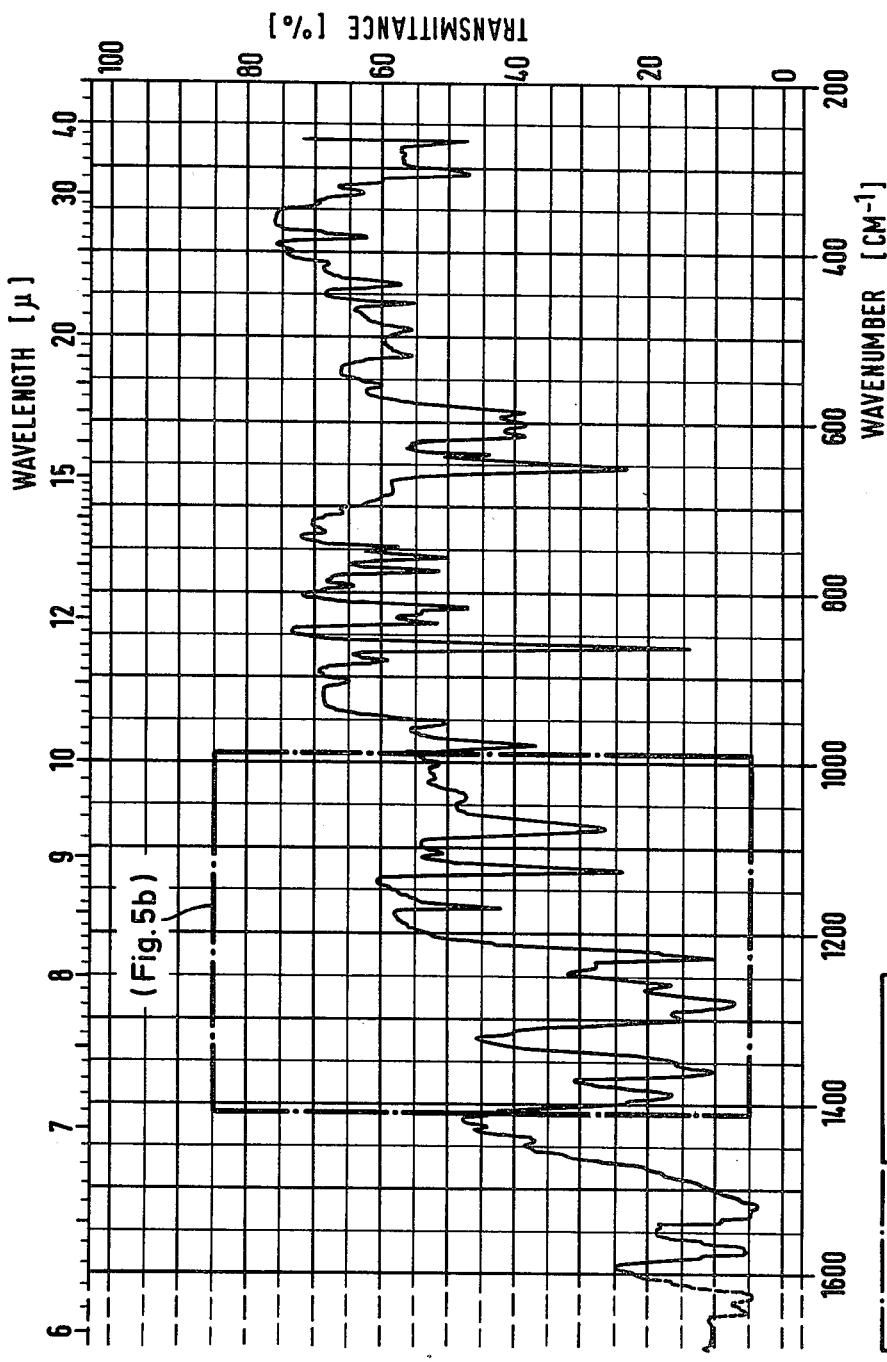
Fig. 5a (II)

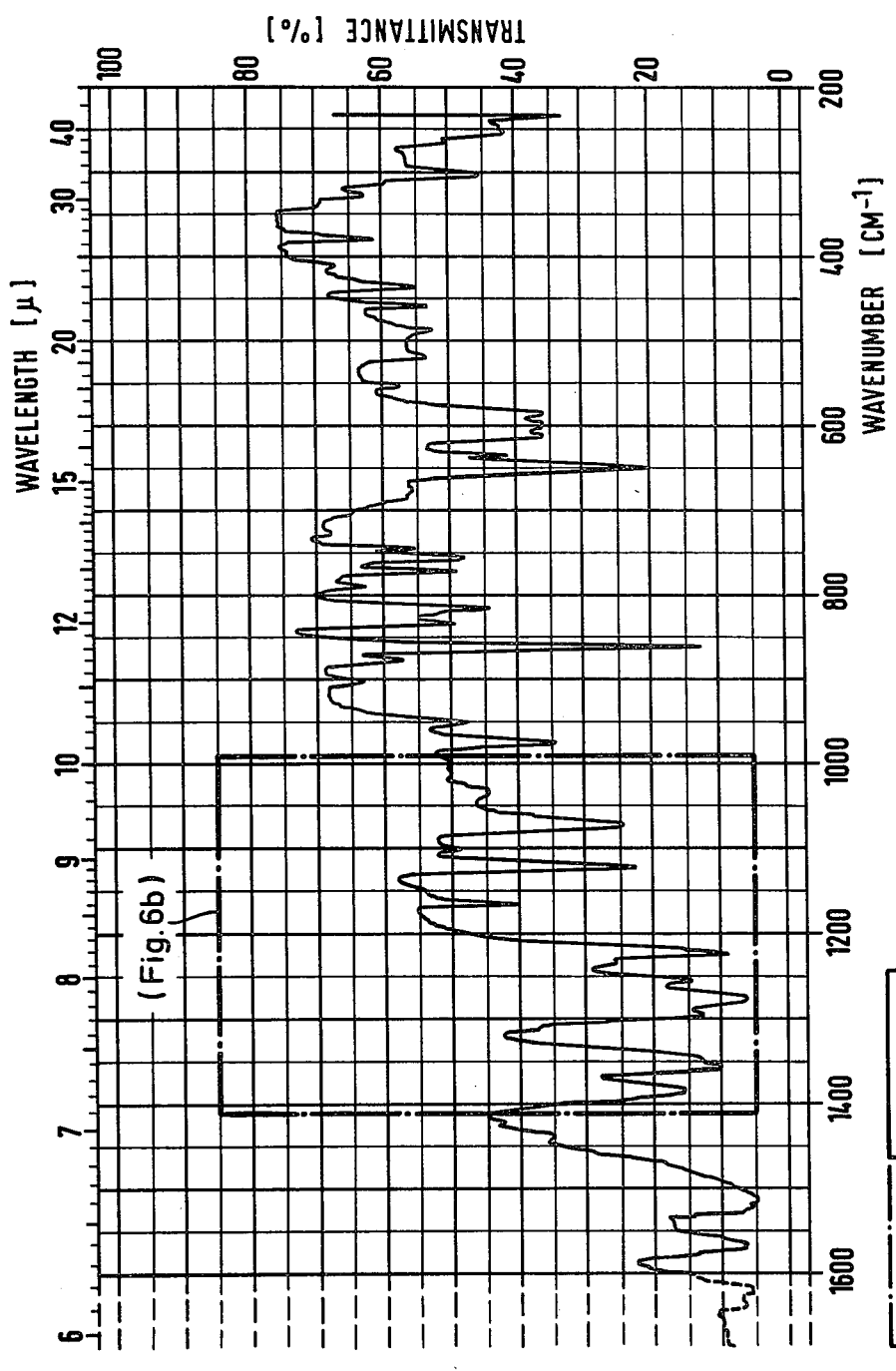
Fig. 6a (II)

2-AMINO-3-CARBETHOXYAMINO-6-(P-FLUORO-BENZYLAMINO)-PYRIDINE-MALEATE

BACKGROUND OF THE INVENTION 2-amino-3-carbethoxyamino-6-(p-fluoro-benzylamino)-pyridine-hydrochloride is described in German Pat. No. 1,795,858, the entire disclosure of which is hereby incorporated by reference. The compound has antiphlogistic and analgesic activity, This hydrochloride is produced by hydrogenating 2-amino-3-nitro-6-(p-fluoro-benzylamino)-pyridine in the presence of Raney nickel at 30 atmospheres absolute and subsequently after the reaction filtering off the catalyst and then reacting the hydrogenated solution with ethyl chloroformate. In the production of the hydrochloride on an industrial scale, however, there are formed intensely blue colored byproducts which can be removed completely only with difficulty or more generally, cannot be removed.

SUMMARY OF THE INVENTION

The invention is directed to 2-amino-3-carbethoxy-amino-6-(p-fluoro-benzylamino)-pyridine-maleate of the formula

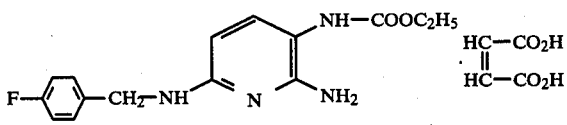

and methods of preparing it as well as uses for it.

The 2-amino-3-carbethoxyamino-6-(p-fluoro-benzylamino)-pyridine-maleate normally consists of a mixture of 2 crystalline modifications A and B wherein the portion of crystal modification A is more than 60%.

2-amino-3-carbethoxyamino-6-(p-fluoro-benzylamino)-pyridine-meleate of the formula

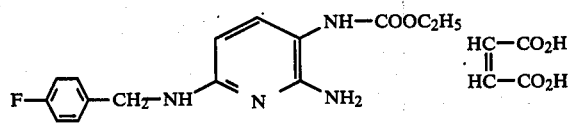

can be prepared by reacting 1 mole of 2-amino-3-carbethoxyamino-6-(p-fluoro-benzylamino)-pyridine in a conventional solvent with 1.1, to 1.5 moles of maleic acid at a temperature between 20° C. and the boiling temperature of the solvent. The reaction temperature is preferably between 20° and 60° C. There is preferably employed as starting material crude 2-amino-3-carbethoxyamino-6-(p-fluoro-benzyl-amino)-pyridine which has been treated with activated carbon and had a melting point of 117°-120° C. In an especially preferred procedure the maleate product is crystallized out of the solvent and heated in the presence of the solvent for 5 to 180 minutes at a temperature between 30° C. and the boiling point of the solvent. In a still more preferred procedure the reaction of the 2-amino-3-carbethoxyamino-6-(p-fluoro-benzylamino)-pyridine with the maleic acid is carried out in the presence of undissolved inoculant crystals at a temperature between 20° and 60° C.

The invention additionally includes a composition useful as a medicine which contains the maleate of the invention together with a customary pharmacological carrier and/or diluent. The medicines have the same uses as the corresponding hydrochloride of German Pat. No. 1,795,858.

2-amino-3-carbethoxyamino-6-(p-fluoro-benzylamino)-pyridine maleate is produced in a simpler and easier manner for the required purity in a medicine than is the hydrochloride Furthermore, the maleate of the invention is particularly well suited for the production of pharmaceutical preparations and has a very good compatability, e.g. with other medicines.

The 2-amino-3-carbethoxyamine-6-(p-fluoro-benzylamino)-pyridine-maleate under the usual conditions is isolated as a mixture of 2 crystal modifications, A and B, in which such a mixture has a changing content of the two modifications A and B. Generally the content of modification A, for example, varies between 0 and 50% (the balance in each case in modification B). This type of mixture is obtained generally in the production in the form of cotton wadding, or felt.

Furthermore it was found that the mixture of the two crystal modifications A and B with a content of modification A between 0 and 50% (the balance in each case consisting of modification B) obtained in the production of the maleate in the customary manner, can be changed in the composition of components A and B through specific procedures so that now for example, reproducible mixtures can be obtained with contents of modification A of 60 to 90%, preferably 65 to 85% (the balance being modification B)

Such a mixture having a content of crystal modification A between 60 and 90% accumulates as non-felted short needles which can be better isolated industrially (for example, they are better and more rapidly filterable).

The crystal modification A of the 2-amino-3-carbethoxyamino-6-(p-fluoro-benzylamino)-pyridine-maleate or maleate mixtures which are enriched in modification A (content of modification A for example 60% to 90%) surprisingly have advantages in regard to the further processing, particularly in regard to galenical processing to a medicine compared to the B-modification or compared to mixtures whose content of modification B is higher than 40%, for example, 50% or more These advantages are as follows:

1. The crystals have a better flowability in the dry state.
2. In mechanical filling there is needed a substantially lower amount of lubricant (e.g. magnesium stearate)
3. The crystals have an improved wettability.

Advantageous maleate mixtures enriched in modification A are for example those having a modification A content between 70 and 85%, preferably 75 to 85%, especially 78 to 82%.

The production of 2-amino-3-carbethoxyamino-6-(p-fluoro-benzylamino)-pyridine-maleate of the invention takes place by reacting 1 mole of 2-amino-3-carbethoxyamino-6-(p-fluoro-benzylamino)-pyridine with 1.1 to 1.5, preferably 1.1 moles, of maleic acid (suitably under a nitrogen atmosphere) with stirring in a conventional solvent at a temperature between 20° C. and the boiling temperature of the solvent used.

Suitably this maleate production takes place at a temperature between 20° C. and 60° C., for example, between 25° C. and 55° C., preferably between 20° C. and 50° C., whereby the maleate crystallizes out at a temperature below 50° C. Hereby there forms for example, a mixture of the two crystal modifications A and B with changing content, for example, the content of modification A is between 0 and 50%, (the balance is modification B).

By heating the thus obtained suspension to from 30° C. to the boiling point of the organic solvent used for the production of maleate (for example from 40° to 130° C. or 40° to 100° C., especially from 50° to 80° C., preferably to 60° to 70° C. for 5 to 180 minutes (for example 20 to 120 minutes) there obtained a maleate mixture in which the A crystal modification predominates and is present in an amount of at least over 60%. Generally in this way there is obtained a maleate mixture having a content of the A crystal modification of 60 to 90% modification A. The remaining portion of the maleate mixture consists of B-crystal modification.

In order to obtain a maleate favorable for further treatment (that is a maleate having a portion of modification A of more than 60%), the concentration of the 2-amino-3-carbethoxyamino-6-(p-fluoro-benzylamino)-pyridine and maleic acid in the solvent used should be so chosen considering the reaction temperature that immediately after the joint addition of base and maleic acid the crystallization of the maleate begins For example, there is employed a solution of pyridine base in isopropanol or ethanol, which for example contains 1 kg of pyridine base in 35 to 38 liters of isopropanol or ethanol. The corresponding amount of maleic acid (1.1 to 1.5 moles based on 1 mole of base) is suitably added as a solution in the same solvent, whereby there are preferably used solutions in isopropanol or ethanol which contain 1 kg of maleic acid in 7 to 9 liters of these alcohols.

If the reaction of the 2-amino-3-carbethoxy-amino-6-(p-fluoro-benzylamino)-pyridine with maleic acid takes place at a temperature which is higher than 60° C. then there is generally obtained a maleate which concists of pure modification B or which is enriched in modification B and which cannot be changed into modification A or a mixture having a predominating content of modification A or which can only be changed with difficulty to modification A or a mixture having a predominant amount of modification A.

As solvents for the production of the maleate there can be used for example lower aliphatic $C_1$–$C_6$ alcohols, e.g. alkanols form methanol to hexanol (preferably with at least 2 carbon atoms such as ethanol, isopropanol, propanol, butanol, sec. butyl alcohol, t-butyl alcohol, pentanol, hexanol, hexanol-2), saturated cyclic ethers (e.g. dioxane, tetrahydrofurane), dipolar aprotic agents such as amides, $C_1$–$C_4$-alkylamides or $C_1$–$C_4$-dialkylamides of aliphatic $C_1$–$C_4$ carboxylic acids (e.g. dimethyl formamide, dimethyl acetamide, diethyl formamide, dibutyl formamide, diethyl acetamide, dimethylbutyramide, methyl formamide, methyl acetamide, butyl acetamide) tetramethyl urea, sulfolane, or dimethyl sulfoxide. These solvents can also be used as mixtures with each other. Likewise, it is possible to use mixtures of such solvents with water.

To remove a blue coloration which may occur in a given case, the base is set free from the thus obtained crude maleate in the customary manner, in which case the operation is suitably carried out under nitrogen. This base is then dissolved in a customary solvent (e.g. isopropanol, ethanol, methanol), treated with 3 to 12, preferably 5 to 10, weight percent of activated carbon (based on the base) and heated for short time, 5 to 20 minutes, preferably 10 minutes) to 50° to 80° C., preferably 65° to 70° C. Then the carbon is filtered off. The precedingly stated carbon treatment can also be combined with a recrystallization. This means the 2-amino-3-carbethoxy-6-(p-fluoro-benzylamino)-pyridine is recrystallized in the presence of the same amount of activated carbon from one of the above-mentioned solvents, optionally with addition of water (suitably under a nitrogen atmosphere), whereby the solvent should be in contact with the carbon a maximum of 10 minutes before the filtration. Preferably this type of recrystallization takes place from isopropanol. As activated carbon there can be used for example activated plant-wood carbons which are produced by activation with pure steam and in a given case, brought to a very low ash content through subsequent treatment with mineral acid (e.g. sulfuric acid or hydrochloric acid) and deionized water, that is vegetable activated carbon which is characterized by low total ash content through a low heavy metal content. Such carbon powder for example, fulfills the requirements of the DAB8 (West) (DAB-Deutsches Arzneibuch, 8th edition of 1978). Polycyclic hydrocarbons are not detectable within the prescribed limits. For example, there are suited medicinal carbon powders according to DAB8 (West) having the following pore distribution.

Micropores (diameter 0–20 Angstroms): 0.6 ml/g
Mesopores (diameter 20–300 Angstroms): 0.15 ml/g
Macropores (diameter greater than 300 Angstroms): 0.5 ml/g Furthermore, there can be used washed (that is subsequently treated with mineral acid and deionized water) and pulverized decolorizing activated carbons which fulfill the requirements of DAB8 in regard to ash content, heavy metal content and fluorescing materials and which are not so finely pored as the medicinal carbons. These types of decolorizing activated carbon for example have the following pore distribution.

Micropores: 0.2–0.4 ml/g, especially 0.4 ml/g
Mesopores: 0.2–0.5 ml/g, especially 0.2 ml/g
Macropores: about 0 5 ml/g, especially 0 5 ml/g.

Such decolorizing activated carbons are produced for example by Degussa Aktiengesellschaft and are available commercially under the registered trademarks Eponit (for example Eponit 114 Spezial, Epopit 113 Special, carbons neutralized with phosphoric acid such as Eponit 113 Np, Eponit 114 Np) and Carbopuron.

If the maleate is produced again in the manner previously described from this base treated with carbon, then there no longer is shown the blue coloration.

The base is set free from the crude maleate in known manner for example, by treating the maleate in a solvent such as those given above for the production of the maleate (preferably isopropanol or ethanol) with ammonia, tertiary amines (lower trialkyl amines such as triethylamine), alkali carbonates, e.g. sodium carbonate or potassium carbonate, alkali hydroxides, e.g. sodium hydroxide or potassium hydroxide, at at temperature between 10° and 40° C., preferably 20° to 30° C., especially 20° to 25° C.

A mixture having a crystal modification A content between 60 and 90% for example, also can be obtained if the reaction of the 2-amino-3-carbethoxyamino-6-(p-fluoro-benzylamino)-pyridine with maleic acid is carried out in the presence of undissolved inoculant crystals. Preferably there used hereby as inoculant crystals such as the A-modification or crystals of a mixture enriched in modification A. The thus obtained mixture for example can likewise contain between 60 and 90%, for example 70 to 85% of modification A. To carry out the process for example there is treated a solution of 1 mole of 2-amino-3-carbethoxyamino-6-(p-fluoro-benzylamino)-pyridine in one of the solvents set forth above, preferably ethanol or isopropanol, at 20° to 80° C. (for example at 25° to 70° C.), especially 25° to 60° C., under stirring with a mixture of 1.1 to 1.5 moles, preferably 1.1 moles of maleic acid in the same solvent in which there are mixed undissolved inoculant crystals, preferably of modification A or inoculant crystals of a mixture as stated above enriched in A (60 to 90% A). The temperature of the mixture can be between 20° C. and 80° C., for example, between 25° C. and 70° C., preferably between 25° C. and 60° C. Then the mixture is immediately cooled to 0° to 25° C., preferably 5° to 15° C., especially 8° C. and the crystallized material centrifuged off.

Furthermore, there can be converted any maleate mixture, for example a maleate mixture obtained in a customary manner with a preponderant portion of modification B (for example, 90 to 55% B) or a maleate mixture having a high A portion (for example 60 to 90% A) by heating without solvent to temperatures between 40° and 180° C., preferably 80° to 150° C., especially 80° to 130° C. in a mixture with a larger content of modification B (11–100% B) or even pure modification B.

Suitably the mixture is held hereby in continuous mechanical movement (for example by shaking). The duration of such a conversion for example can be between 10 minutes and 14 days. The starting maleate mixture employed is obtained for example by the already described reaction of 2-amino-3-carbethoxyamino-6-(p-fluoro-benzylamino)-pyridine with maleic acid, in a given case precipitation of the maleate by addition of water, centrifuging off or filtering off of the maleate and drying the same in a vacuum at room temperature.

BRIEF DESCRIPTION OF THE DRAWING

FIGS. 1 through 7c are IR spectra.

DETAILED DESCRIPTION

Properties of the crystal modification B as well as of the mixture of the two crystal modification A and B.

Modification B

M.P. 177.7°–177.8° C.: (Mettler FP-1-Apparatus)
177.3° C.: (Differential Calorimetry)

Figure 2A:
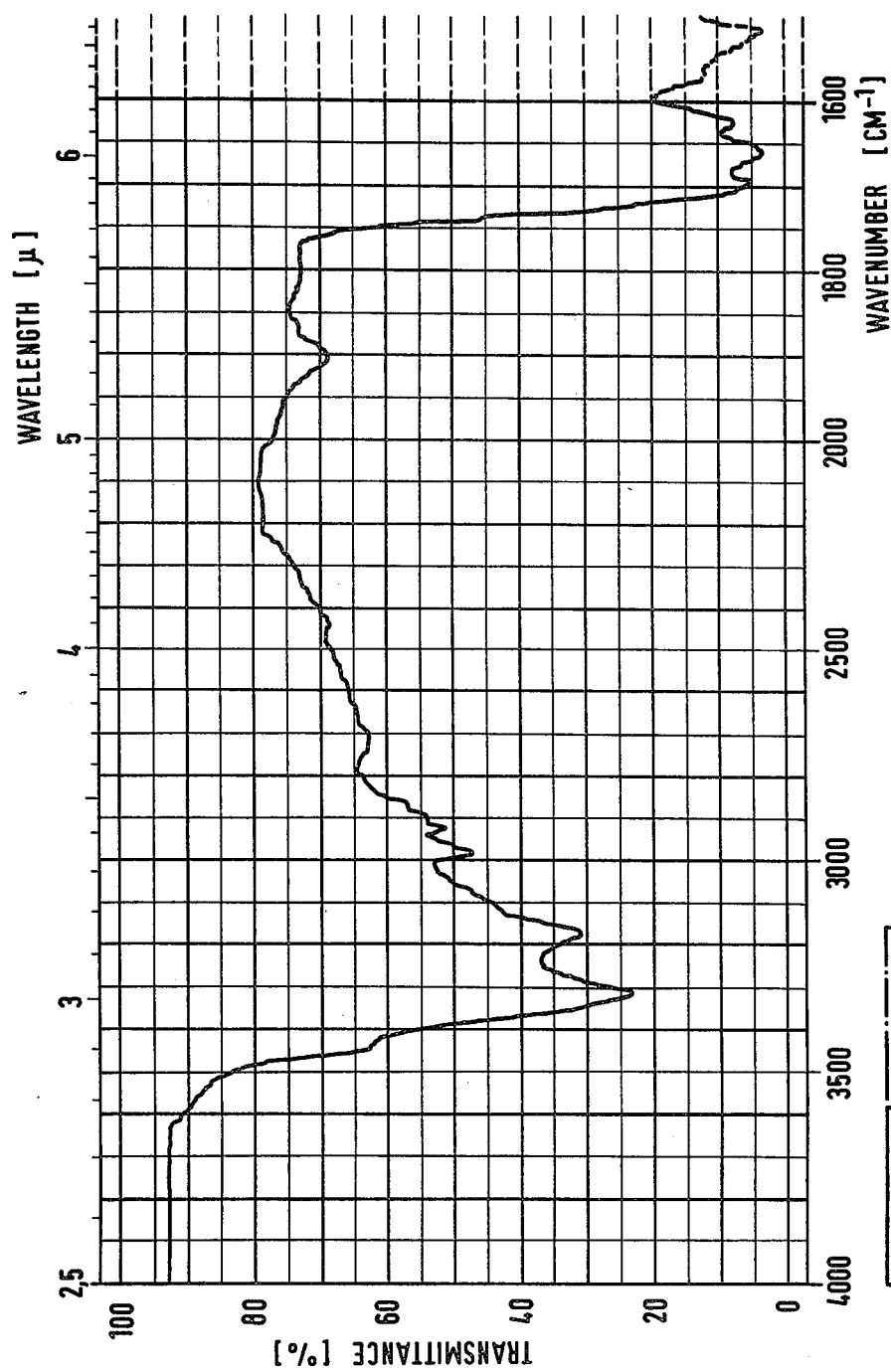
Figure 2B:
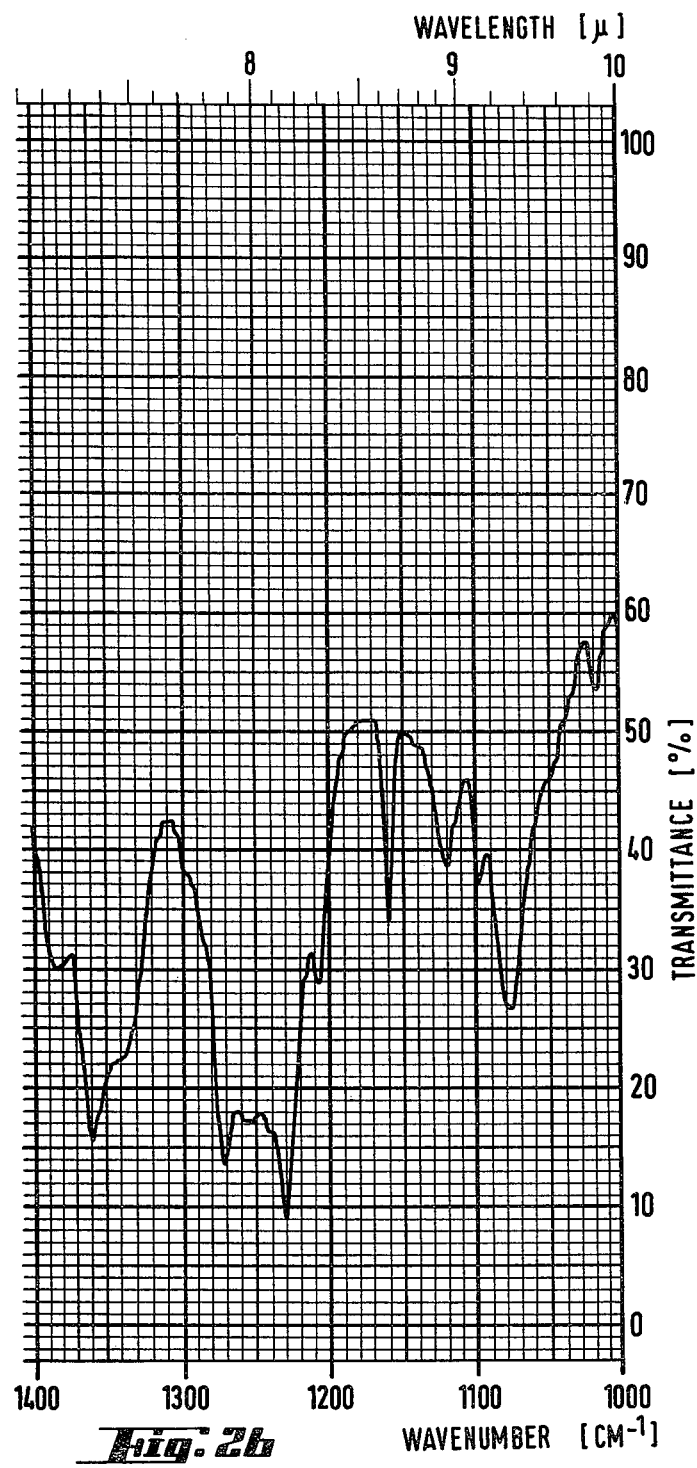

The IR spectrum in KBr is set forth in the drawings FIG. 2a (I, II) and 2b. FIG. 2b is an enlarged section of the spectrum according FIG. 2a in the region between 1100 and 1200 cm$^{-1}$ in which in each case there lie the characteristic bonds for modifications A and B. The analogy is also true for all spectra with the additional designation b.

Maxima in the IR-Spectrum 3318, 3179, 1691, 1658, 1512, 1348, 1270, 1229, 1158 1120, 1071, 861, 821, 779, 650 cm$^{-1}$

Description of the Mettler-FP-1-Apparatus

According to definition the melting point is the temperature at which a material changes from the solid into the liquid condition. Thereby most materials change their optical properties. In the Mettler -FP-1 the samples are illuminated by a light source. Photo cells respond to the increase in transmission of light of the sample material in the melting and through this solve the integrating device result. The sample tubes are fixed in a heated metal cylinder. Its temperature increase is continuously and linearly electrically controlled with a preselectable gradient. A mechanical integrating device indicates the momentary oven temperature in digital form; three secondary integrating devices fix the melting point.

The characterization of modification A and B as well as the determination of the portions of these modifications in the mixtures takes place for example through the quantitative IR- spectroscopic analysis described below.

Principle of the Method 2-amino-3-carbethoxyamino-6-(p-fluorobenzylamino)-pyridine-maleate consists of a mixture of crystal modifications A and B. Modification A and B differ strongly in their IR spectra. For the quantitative determination of the portions of A and B there is suited a double band at 1160 and 1170 cm$^{-1}$. The pure modification B is characterized by a band at 1160 cm$^{-1}$; the pure modification A by a band at 1170 cm$^{-1}$. Mixtures consisting of modification A and B are characterized according to their composition by the simultaneous occurrence of both bands, in each case in weakened form. From the relative heights of the bands there can be calculated the portion of A or B.

The significance of crystal modification B among others also is that with its help the exact contents of modification A and B can be determined as is set forth below.

Production of the KBr Blank (This production of the blanks is valid for all IR spectra in the application.)

In mixing and grinding KBr with 2-amino-3-carbethoxyamino-6-(p-fluoro-benzylamino)-pyridine-maleate without a solvent there can take place a change of modification A into modification B. Therefore it is necessary to produce the KBr blank exactly according to specification.

Weighed portion: 0.8 to 1.0 mg of 2-amino-3-carbethoxyamino-6-(p-fluoro-benzylamino)-pyridine-maleate and 300 mg KBr.

Grinding out Mixing: Electromechanical ball mill having a power input of 300 volt amperes (Perkin Elmer), chrome steel capsule having a steel ball.

Duration of grinding: up to 15 seconds, sepecially 10 to 15 seconds. A duration of grinding of more than 15 seconds should be avoided.

Pressing: 13 mm pressing tool SPEAC F. Oriel
Deaeration: 2 minutes at 5 Torr
Pressing: 2 minutes with 8 tons (metric tons)

IR Absorption and Evaluation

Apparatus: Perkin Elmer Lattice spectrophotometer 521
Ordinate elongation: 1x
Slit program: 10
Gain: about 3
Attenuator Speed: 11
Scan Time: 2/2
Suppression: 5
Signal Ampl. amplified response: 3

In order to enlarge the bands for the purpose of better evaluation a louved screen is placed in the comparison ray and the ordinate adjusted to 90 to 100% transmission or 0.0 to 0.01 extinction at 1140 cm$^{-1}$ and subsequently the region from 1220 to 1130 cm$^{-1}$.

To evaluate the height of the bands the two minimum at 1180 and 1140 cm$^{-1}$ are joined together and there is measured the band height at 1170 and 1160 up to this combination line.

Figure 7A:
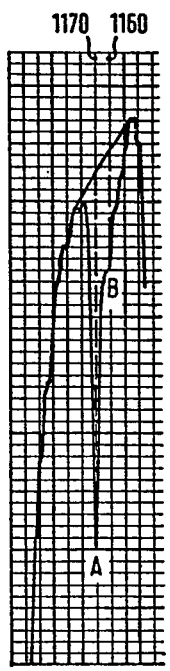
Figure 7B:
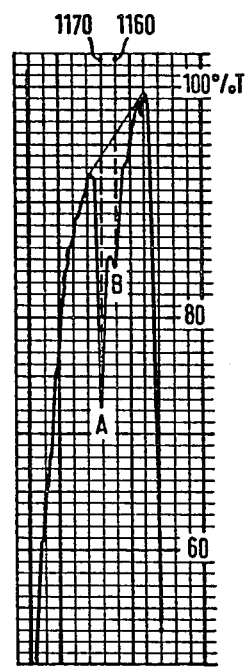
Figure 7C:
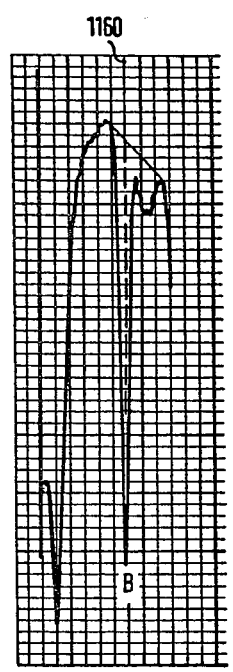

FIGS. 7a and 7b show the IR spectrum of a mixture containing 85% A (and accordingly 15% B) between 1100–1200 cm$^{-1}$ and FIG. 7c the IR spectrum of the pure modification B between 1100–1200 cm$^{-1}$.

The calculation of the content of a mixture of modification A based on the spectrum for the pure modification B (see FIG. 7c as well as FIG. 2b) takes place according to the following formula:
Content of crystal modification A in %

$$\frac{h_A \cdot 100}{h_A + h_B}$$

$h_A$ = height of bands at 1170 cm$^{-1}$;
$h_B$ = height of bands at 1160 cm$^{-1}$
Standard deviation $s_A$ = 5%

Maleate mixtures with different contents of the two crystal modifications A and B besides being characterized by the IR spectrum can also be characterized by a definite melting range. Below there are given several melting ranges for this type of mixture of specific compositions (determination of the melting point took place with the Mettler FP-1 apparatus):

| | M.P. °C. |
|---|---|
| 84% A–16% B | 175.5–176.0 |
| 77% A–23% B | 175.6–176.0 |
| 71% A–29% B | 176.5–176.7 |
| 56% A–44% B | 177.0–177.3 |
| 48% A–52% B | 176.4–177.0 |
| 31% A–69% B | 177.0–177.0 |
| 0% A–100% B | 177.7–177.8 |

Unless otherwise indicated all parts and percentages are by weight.

The process can comprise, consist essentially of, or consist of the steps set forth with the stated materials.

The 2-amino-3-carbethoxyamino-6-(p-fluoro-benzylamino)-pyridine used for the production of the maleate of the invention can be obtained starting from 2,6-dichloro-3-nitro-pyridine via 2-amino-3-nitro-6-chloro-pyridine (see German Pat. No. 1,795,797 and related Steinmetz U.S. Pat. No. 3,809,695, the entire disclosure of which is hereby incorporated by reference) and further reaction of the latter compound with p-fluoro-benzylamino subsequent reduction of the nitro group to the amino group and acylation of the amino group with ethyl chloroformate in known manner for this type of reaction (see Belgian Pat. No. 698,384 and related Thiele U.S. Pat. No. 3,481,943 and Belgian Pat. No. 764,362, the entire disclosure of which are hereby incorporated by reference). In case the reaction with ethyl chloroformate is not carried out in the presence of a basic material there is obtained the hydrochloride from which the base can then be obtained by treating with basic materials (for example tertiary amines such as triethylamine). For example, there can be used the following procedures.

There were led into a solution of 21.3kg of 2,6-dichloro-3-nitropyridine (90%, water wet) in 100 liters of isopropanol with stirring at 20°–30° C. 6.8 kg (400 moles) of ammonia gas (there can also be dropped in liquid ammonia). Then stirring was carried out for 24 hours at room temperature. The 2-amino-3-nitro-6-chloro-pyridine formed was further reacted in suspension after the testing for unreacted 2,6-dichloro-3-nitro-pyridine by means of thin layer chromatography or gas chromatography is negative.

There was run into the suspension of 2-amino-3-nitro-6-chloro=pyridine at room temperature with stirring a solution of p-fluoro-benzylamine in isopropanol (see additionally below). Subsequently there were dropped in 22.3 kg of triethylamine and the mixture stirred under reflux for 6 hours. Thereupon there were run in 100 liters of water and the compound 2-amino-3-nitro-6-(p-fluoro-benzylamino)-pyridine crystallized out. It was filtered off with suction, washed with isopropanol and dried (Yield: 21 kg, M.P.: 179°–181° C.).

The p-fluoro-benzylamine solution is obtained for example, as follows:

A solution of 18.6kg of p-fluorobenzaldehyde in 60 liters of isopropanol is treated in an autoclave under nitrogen with 4kg of Raney nickel. There is led in 10.2kg of ammonia and the closed autoclave heated with stirring for 3 hours at 80° C. Then it was rinsed with nitrogen and hydrogenated with 5 to 10 bar of hydrogen at 50°–65° C. After the end of the hydrogen uptake stirring was continued for 1 hour more, the catalyst filtered off; the thus obtained solution directly further processed.

17.6kg of the thus obtained 2-amino-3-nitro-6-(p-fluoro-benzylamine)-pyridine was hydrogenated in 60 liters of dioxane with addition of 12 kg of magnesium sulfate and 2 kg of Raney nickel at 2 to 30 bar and 60°–80° C. The solution was filtered under careful exclusion of air. After addition of a further 30 liters of dioxane (serving to wash the filter cake) there were dropped into the filtrate under nitrogen 7.7 liters of ethyl chloroformate as well as 11.7 liters of triethylamine under cooling; an exothermic reaction occurred. The temperature increased to about 75° C. Subsequently the mixture was stirred for a further 2 hours. When the internal temperature reaches 30° C. the cooling water is stopped.

The isolation of the 2-amino-3-carbethoxy-amino-6-(p-fluoro-benzylamino)-pyridine takes place for example via the maleate: The hydrogenated mixture obtained as stated above is filtered via a pressure filter and mixed with 510 liters of isopropanol at 25° C. There were added a further 30 liters of isopropanol which was used to wash the filter cake. The solution of the hydrogenated mixture was then treated with a warm solution of 12 kg of maleic acid in 60 liters of isopropanol with stirring (suitably in several batches).

The corresponding maleate immediately precipitated. The pH value is checked in each case and should be 3 to 4. The thus obtained suspension is cooled to about 20° C., centrifuged and washed with 30 liters of isopropanol. The thus obtained crude maleate can be changed into a mixture enriched in modification A (for example, 60 to 90% modification A) by subsequent heating (for example, in isopropanol) as previously set forth, whereby the subsequent heating in a given case is repeated up to two times. However, the following further processing is more favorable: The crude maleate obtained as described above (32.66 kg, wet with isopropanol, 74.5%) is converted into the free base with 20 liters of aqueous concentrated ammonia in a stirring apparatus in which there are present 50 liters of isopropanol. Thereby alternatingly the maleate and the ammonia are poured in. The operation was carried out under nitrogen. After all of the maleate and ammonia are added there were added 61 liters of water and stirring continued for a further hour. The free base of 2-amino-3-carbethoxyamino-6-(p-fluoro-benzylamino)-pyridine was centrifuged off, washed neutral with water and dried in a vacuum at 55° C. The crude base had a melting point of 117° to 120° C. The thin layer chromatogram (mobile phase methanol/chloroform 8:2) showed a main spot $R_f$ 0.72 as well as two traces of minor spots $R_f$ 0.78 and 0.80. The IR spectrum in KBr (FIG. 1, I and II) shows maxima at: 3371, 3360, 3200, 2982, 1698, 1621, 1505, 1425, 1286, 1255, 1220, 1162, 1105, 1073, 850, 838, 803, 584, 497 cm$^{-1}$. The IR spectrum does not change if this crude base is treated with activated carbon as stated at the outset (for example 10 minutes in isopropanol at 50° to 60° C.); merely the two minor spots in the thin layer chromatogram were still weaker and the melting point is now after previous sintering (115° C.) at 117° C.

A 5% solution of ethanol still shows green coloration which is increased within 12 hours after the introduction of air.

The thus obtained crude base of the 2-amino-3-carbethoxyamino-6-(p-fluoro-benzylamino)-pyridine after the already described purification with activated carbon can be employed directly for the production of the colorless maleate. Likewise there can also be employed a crude base obtained in another manner after the already described carbon treatment, whereby hereby generally a larger amount of activated carbon is required than with a crude base obtained from the maleate: For example, if the reaction with the ethyl chloroformate is carried out without the presence of an additional basic material (as for example triethylamine) then there is obtained the hydrochloride of the 2-amino-3-carbethoxyamino-6-(p-fluoro-benzylamino)-pyridine (M.P.: 214°–215° C.), which in a given case can be recrystallized from isopropanol. The crude base is obtained from this hydrochloride by treatment with a basic material (tertiary amini such as triethylamine, alkali carbonate, alkali hydroxide) in a customary solvent or suspension agent. For example, the crude base with a M.P.: 117° to 120° C. can be obtained from the hydrochloride in methanolic solution by addition of aqueous ammonia.

However, the above-described crude base of the 2-amino-3-carbethoxyamino-6-(p-fluoro-benzylamino)-pyridine can be recrystallized instead or also be recrystallized again in the presence of activated carbon. For this purpose 15.9 kg of crude base are dissolved hot at 75° C. in 48 liters of isopropanol under nitrogen, treated with activated carbon and filtered after 10 minutes. Crystallization takes place with occasional stirring The base is centrifuged off, washed with 5 liters of isopropanol, and dried in a vacuum at 55° C. In the thin layer chromatogram (mobile agent methanol/chloroform 8:2) there showed a main spot $R_f$ 0.72 as well as very weak traces of two minor spots ($R_f$ 0.78 and 0.80). The IR spectrum is identical with the IR spectrum of the crude base according to FIG. 1, I and II. A 5% solution in ethanol is colorless, which in the course of 20 hours with the introduction of air is colored green.

The precedingly described base is likewise suited for the production of a pure maleate and the corresponding modification mixture.

The most favorable method of production is the following:

The 2-amino-3-carbethoxyamino-6-(p-fluoro-benzylamino)-pyridine is converted into the maleate as stated. As described the base (crude base) is produced from this maleate. This base is treated as stated with activated carbon and/or recrystallized in the presence of activated carbon. The thus obtained base is now again converted into the maleate as already described (suitably under nitrogen).

The compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared with the usual pharmaceutical excipients, assistants, carriers, and diluents.

As carriers and assistants, for example, are those recommended in the following literature as adjuvants for pharmacy, cosmetic, and related fields such as Ullmann's Encyklopä adie der technischer Chemie, Vol. 4 (1953), pages 1 to 39, Journal of Pharmaceutical Sciences 52 (1963), pages 918 et seq.; H.V. Czetsch-Lindenwald, Hilfsstoffe fur Pharmazie und angrenzende Gebiete; Phar Ind. 2 (1961) pages 72 et seq.; Dr. H. O. Fiedler, Lexikonder Hilfstoffe fur Pharmazie, Kosmetik und angrenzende Begiete, Cantor Kg. Aulendorf i. Wurtt (1971).

Examples of such materials include gelatin, natural sugars such as sucrose or lactose, lecithin, pectin, starch (for example cornstarch), alginic acid, tylose (methyl cellulose), talc, lycopodium, silica (for example colloidal silica), glucose, cellulose, hydroxyethyl cellulose, stearates, e.g. methylstearate and glyceryl stearate, magnesium and calcium salts of fatty acids with 12 to 22 carbon atoms, especially saturated acids (for example, calcium stearate, calcium laurate, magneisum oleate, calcium palmitate, calcium behenate and magnesium stearate), emulsifiers, oils and fats, castor oil, olive oil, sesame oil, cottonseed oil, corn oil, wheat germ oil, sunflower seed oil, cod-liver oil), mono-, di- and triglycerides of saturated fatty acids ($C_{12}H_{24}O_2$ to $C_{18}H_{38}O_2$ and their mixtures), e.g. glyceryl monostearate, glyceryl distearate, glyceryl tristearate, glyceryl trilaurate, pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and and unsaturated fatty acids 2 to 22 carbon atoms, especially 10 to 18 carbon atoms), with monohydric aliphatic alcohols (1 to 20 carbon atom alkanols) or polyhydric alcohols such as glycols, glycerine, diethylene glycol, pentaerylthritol, sorbitol, mannitol, ethyl alcohol, butyl alcohol, octadecyl alcohol, etc. e.g., glyceryl stearate, glyceryl palmitate, glycol distearate, glycol dilaurate, glycol diacetate, monoacetin, triacetin, glyceryl oleate, ethylene glycol stearate, such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g. ethyl lactate, ethyl carbonate, silicones (especially middle viscosity dimethyl polysiloxane), magnesium carbonate and the like.

For the production of solutions there can be used water or physiologically compatible organic solvents, as for example, ethanol, 1,2-propylene glycol, polyglycols, e.g. diethylene glycol, triethyl glycol, and dipropylene glycol and their derivatives, dimethyl sulfoxide, fatty alcohols, e.g. stearyl alcohol, cetyl alcohol, lauryl alcohol and oleyl alcohol, triglycerides, e.g. glyceryl oleate, glyceryl stearate, glyceryl palmitate, and glyceryl acetate, partial esters of glycerine, e.g., monoacetic, diacetin, glyceryl monostearate, glyceryl distearate, glyceryl monopalmitate, paraffins and the like.

In the production of the preparation there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxyethylated sorbitan monoleate, polyoxyethylated fats, polyoxyethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerization generally is between 2 and 40, particularly between 10 and 20.

Such polyoxyethylated materials for example can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glyceride).

Examples of oleotriglycerides are olive oil, peanut oil castor oil, sesame oil, cottonseed oil, corn oil (see also Dr. H. P. Fiedler, supra, pages 191–195.

Furthermore, there can be added preservatives, stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium meta bisulfite, ascorbic acid, gallic acid, butyl hydroxyanisole, nordihydroguararetic acid, tocopherols, as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxy-benzoic acid esters (for example, lower alkyl esters such as the methyl ester and the ethyl ester), benzoic acid, sodium benzoate, trichloroisobutyl alcohol, phenol, cresol, benzethonium chloride, and formalin derivatives.

The pharmacological and galenical treatment of the compounds of the invention takes place according to the usual standard methods. For example, the active material or materials and assistants or carriers are well mixed by stirring or homogenization (for example, by means of a colloid mill or ball mill) wherein the operation is generally carried out at temperatures between 20° and 80° C., preferably 20° to 50° C.

The application of active material or drug can take place on the skin or muccous membrane or internally, for example, orally, enterally, pulmonarily, rectally, nasally, vaginally, lingually, intravenously, intraarterially, intracardially, intramuscularly, intrapertioneally, intracutaneously or subcutaneously.

The addition of other medicines is also possible.

EXAMPLE 1

Production of the pure crystal modification B of the 2-amino-3-carbethoxyamino-6-(p-fluoro-benzylamino)-pyridine-meleate A solution of 30.0 grams (0.1 mole) of 2-amino-3-carbethoxyamino-6-(p-fluoro-benzylamino)-pyridine (crude base having M.P. 117° C. (sintered at 115° C.)) prepared at 60° C., which was treated for 10 minutes in isopropanol at 50° to 60° C. with activated carbon: $R_f$ 0.72 in methanol/chloroform 8:2; IR in KBr see FIG. 1, I and II; Maxima at: 3371, 3360, 3200, 2982, 1698, 1621, 1505, 1425, 1286, 1255, 1220, 1162, 1105, 1073, 850, 838, 803, 584, 497 cm$^{-1}$ in 1080 ml of isopropanol is treated with a solution of 12.8 grams (0.11 mole) of maleic acid in 96ml of isopropanol at 60°–62° C., which contains inoculant crystals of modification B. The mixture is cooled to 17° C. and the compound crystallized out filtered off. The inoculant crystals of modification B are obtained for example by heating during 2 hours at 150° C. in the dry condtion a maleate mixture obtained according to Example 4.

Yield: 96.6% of theory.
M.P. 177.7°–177.8° C. (Mettler FP-1-apparatus).
IR Spectrum in KBr: see FIG. 2a (I,II) and 2b.

EXAMPLE 2

Production of a 2-amino-3-carbethoxyamino-6-(p-fluoro-benzylamino)-pyridinemaleate with a content of crystal modification A of 80% (±5% limit of error)

30 grams (0.1 mole) of 2-amino-3-carbethoxhamino-6-(p-fluoro-benzylamino)-pyridine (crude base having M.P. 117° C. (sintered at 115° C.)) as in Example 1, $R_f$ 0.72 in methanol/chloroform 8:2; IR in KBr see FIG. 1, I and II; maxima at: 3371, 3360, 3200, 2982, 1698, 1621, 1505, 1425, 1286, 1255, 1220, 1162, 1105, 1073, 850, 838, 803, 584, 497 cm$^{-1}$ were dissolved at 65° C. in 1100 ml of isopropanol, cooled to 25° C. and treated with stirring with a solution of 12.8 grams (0.11 mole) of maleic acid in 98ml of isopropanol at 25° C. The "maleate" resulting as a wad-like precipitate was heated in the suspension present for 60 minutes at 60° C., allowed to cool to 25° C. and centrifuged off.

Yield: 96% of theory.
M.P.: 175.2°–175.7° C. (Mettler FP-1-apparatus).

The thus obtained "maleate" consisted of 80% of crystal modification A and 20% of crystal modification B (limit of error ±5%).

Figure 3B:
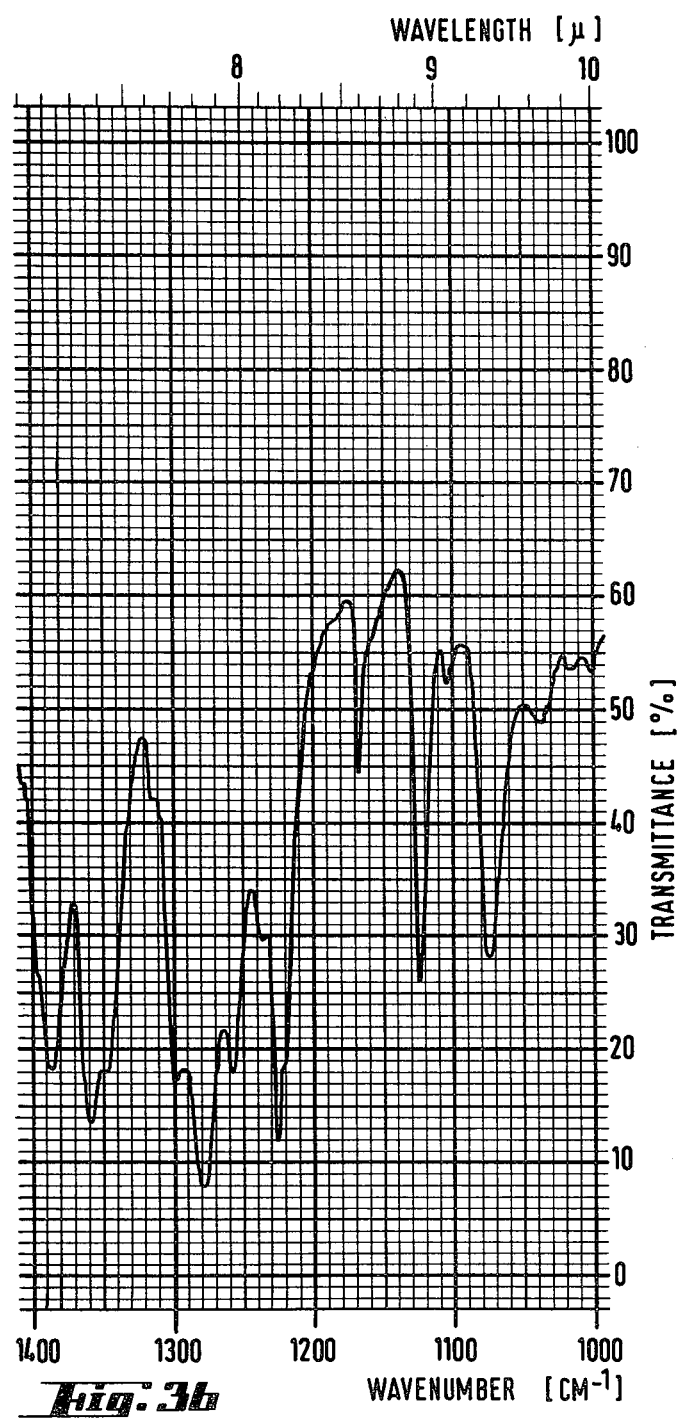

IR Spectrum in KBr see FIG. 3a (I,II) and 3b.

EXAMPLE 3

Production of a 2-amino-3-carbethoxyamino-6-(p-fluoro-benzylamino)-pyridine-maleate having a content of crystal modification A of 71% (±5% error limit)

A solution of 45 grams of 2-amino-3-carbethoxyamino-6-(p-fluoro-benzylamino)-pyridine (base as in Example 2) in 1626 ml of ethanol prepared at 65° C. is treated with a mixture of 18.9 grams of maleic acid in 146 ml of ethanol in which there were admixed undissolved inoculant crystals of a mixture enriched in modification A (content of A=80%, obtained according to Example 2). The mixture was immediately cooled to 8° C. and the compound crystallized out centrifuged off.

Yield: 94.1% of theory.
M.P.: 176.5°–176.7° C. *Mettler FP-1-apparatus).

Figure 4A:
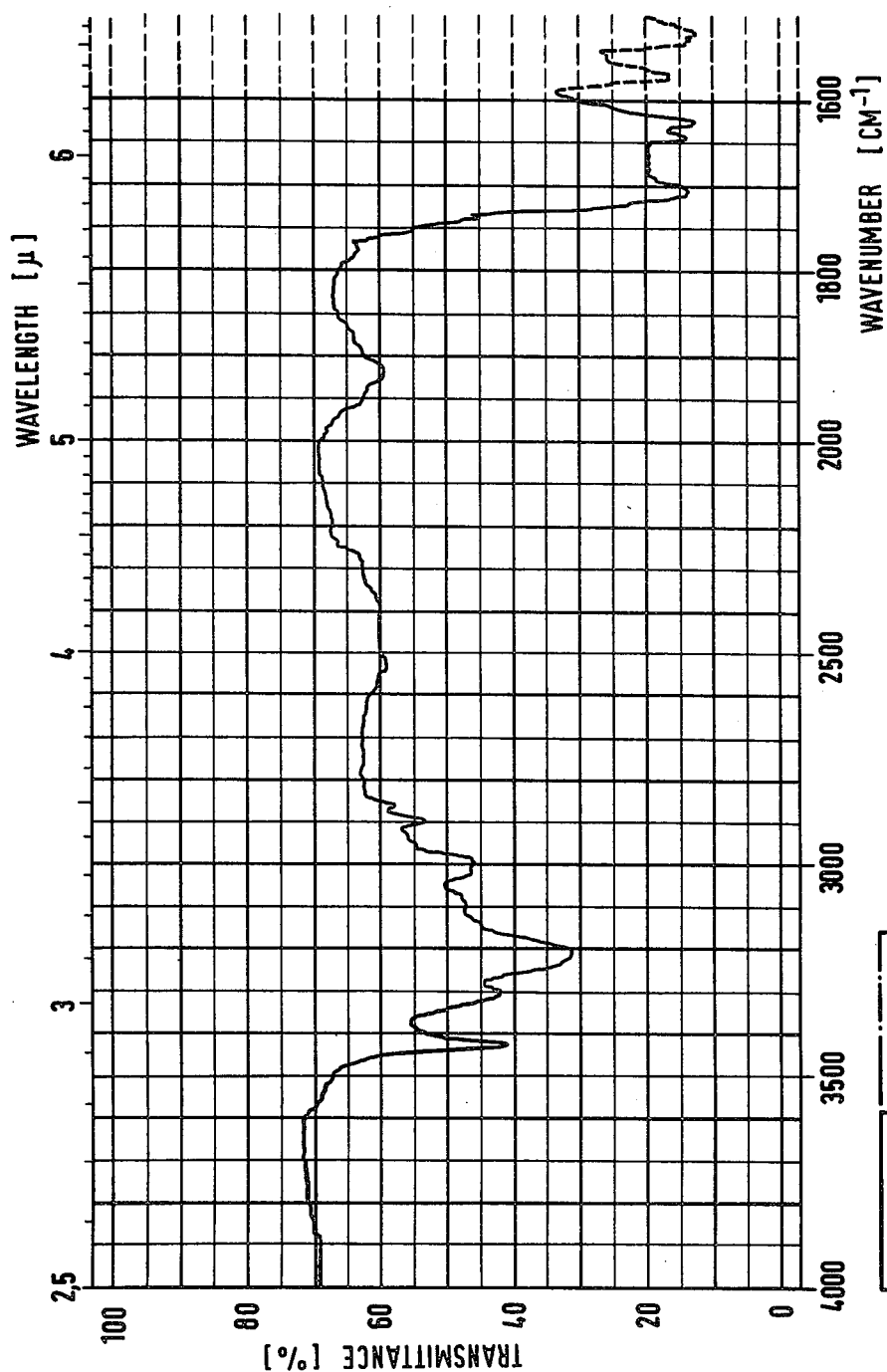
Figure 4B:
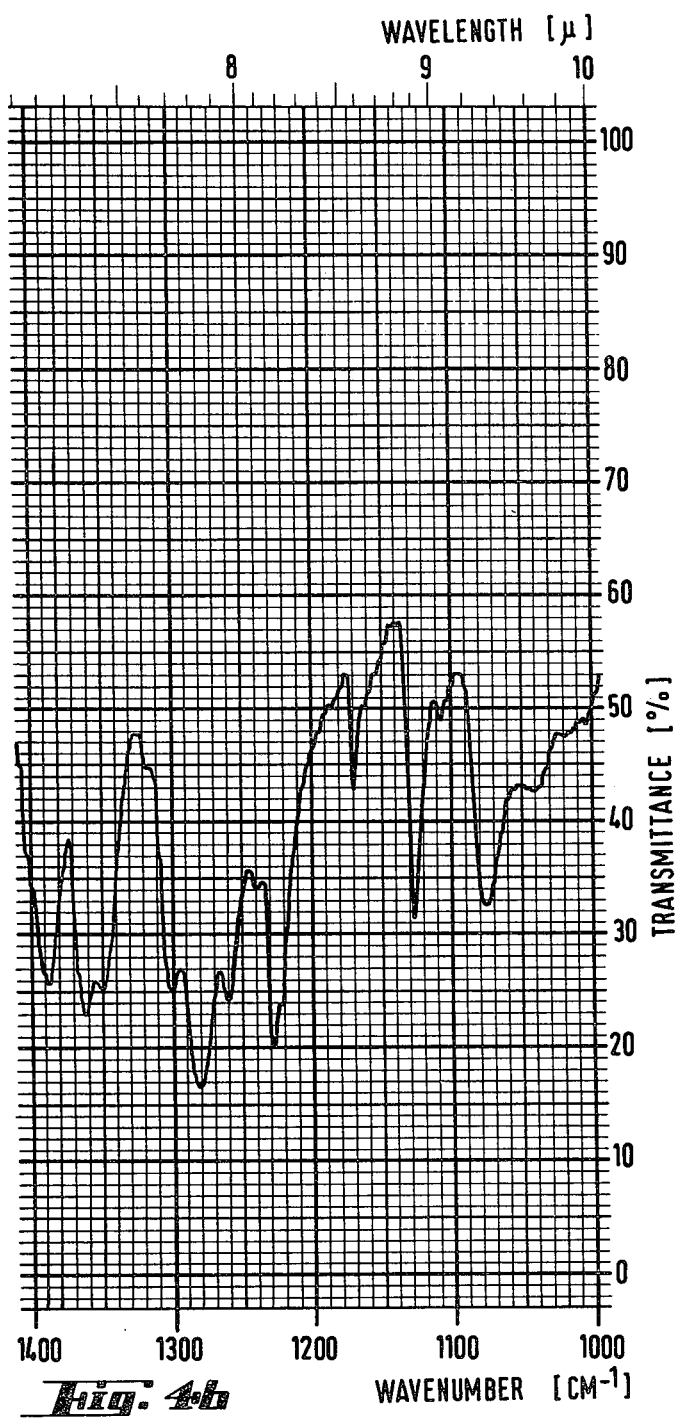

IR Spectrum in KBr see FIG. 4a (I,II) and 4b. Maxima at: 3430, 3300, 3218, 1920, 1710, 1645, 1630, 1571, 1520, 1390, 1362, 1280, 1229, 1170, 1127, 1076, 970, 865, 656 cm$^{-1}$.

EXAMPLE 4

Production of 2-amino-3-carbethoxyamino-6-(p-fluoro-benzylamino)-pyridine-maleate having a content of crystal modification A of 84% (±5% error limit)

In a heatable 500 liter stirred apparatus (Pfaudler apparatus) gassed with nitrogen, there were heated to 50° C. 370 liters of isopropanol, 43.0 kg (141.29 moles) of 2-amino-3-carbethoxyamino-6-(p-fluoro-benzylamino)-pyridine (base as in Example 2) added and the temperature of the mixture raised to 70° C. After addition of a suspension of 4.3kg of activated carbon in 13 liters of isopropanol the solution was held at 70° C. for 10 minutes and filtered under nitrogen pressure via a filter press. The filtrate was immediately led under nitrogen gassing into a 2000 liter stirred apparatus (Pfaudler apparatus) in which there are present 1151 liters of isopropanol. This solution was adjusted to 25° C. and while maintaining this temperature treated under a nitrogen atmosphere with a solution of 18.04 kg maleic acid in 138 liters of isopropanol. The maleate precipitates in a stirrable voluminous form. Heating is carried out for one hour at 60° C., cooled to 18°-20° C., the maleate centrifuged off and washed 3 times, each time with 15 liters of ice cold isoproponal. The isolated compound was dried in a vacuum at 50° C.

Yield: 95% of theory.

The thus obtained maleate consisted of 84% crystal modification A and 16% crystal modification B.

M.P.: 175.5°-176.0° C. (Mettler-FP-1-apparatus).

Figure 5B:
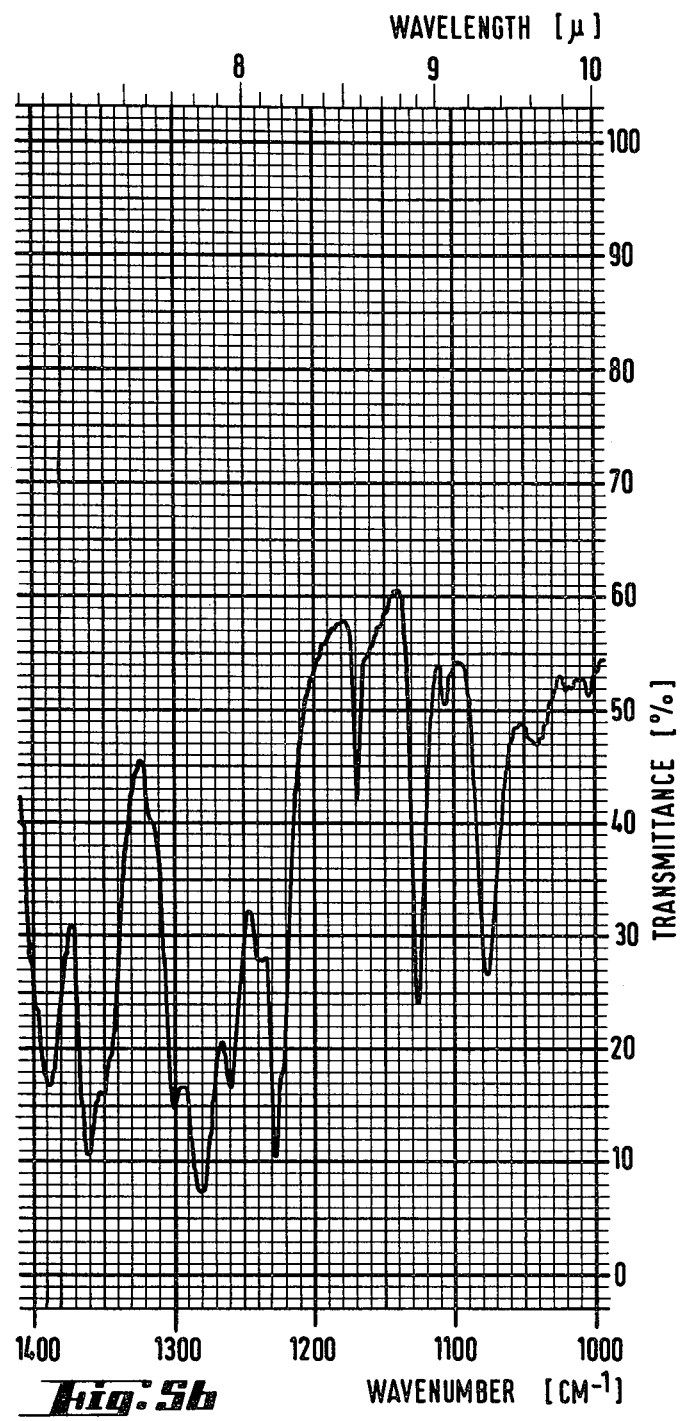

IR Spectrum in KBr see FIG. 5a (I,II) and 5b. Maxima at 3430, 3300, 3218, 1920, 1710, 1645, 1626, 1571, 1520, 1390, 1361, 1280, 1229, 1170, 1126, 1076, 970, 855, 653 cm$^{-1}$.

EXAMPLE 5

Production of a 2-amino-3-carbethoxyamino-6-(p-fluoro-benzylamino)-pyridine-maleate having a content of crystal modification A of 77% (±5% error limit)

A solution of 45 grams of 2-amino-3-carbethoxyamino-6-(p-fluoro-benzylamino)-pyridine (base as in Example 2) in 1626 ml of isopropanol prepared at 60° C. is treated with a mixture of 18.9 grams of maleic acid in 146 ml of isopropanol in which there were admixed undissolved inoculant crystals of maleate mixture entriched in modification A (80% modification A obtained according to Example 2). Cooling to 18° C. was carried out immediately and the compound crystallized out was centrifuged.

Yield: 94.1% of theory.

M.P.: 175.6°-176.0° C. (Mettler-FP-1-content).

Figure 6A:
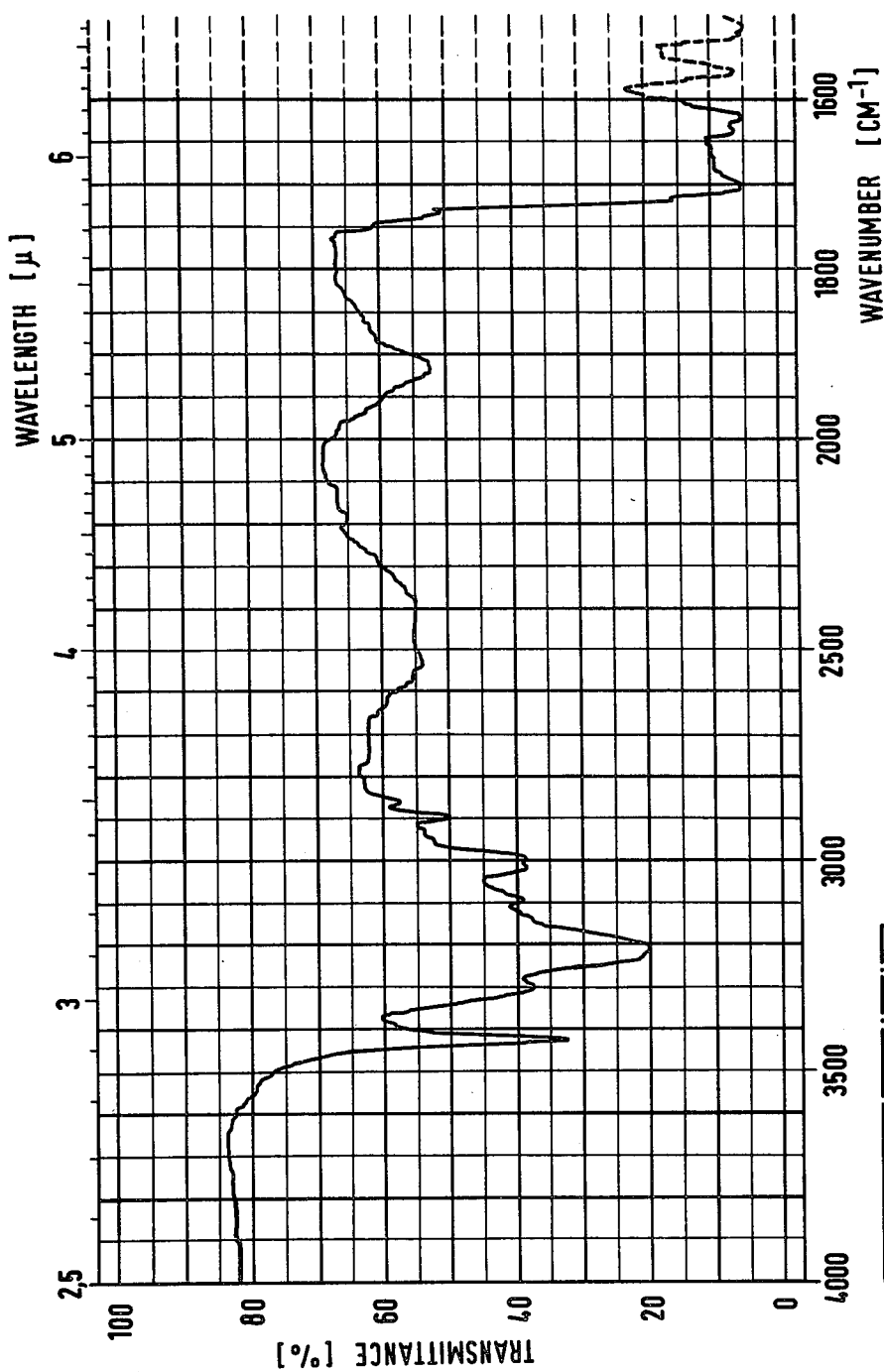
Figure 6B:
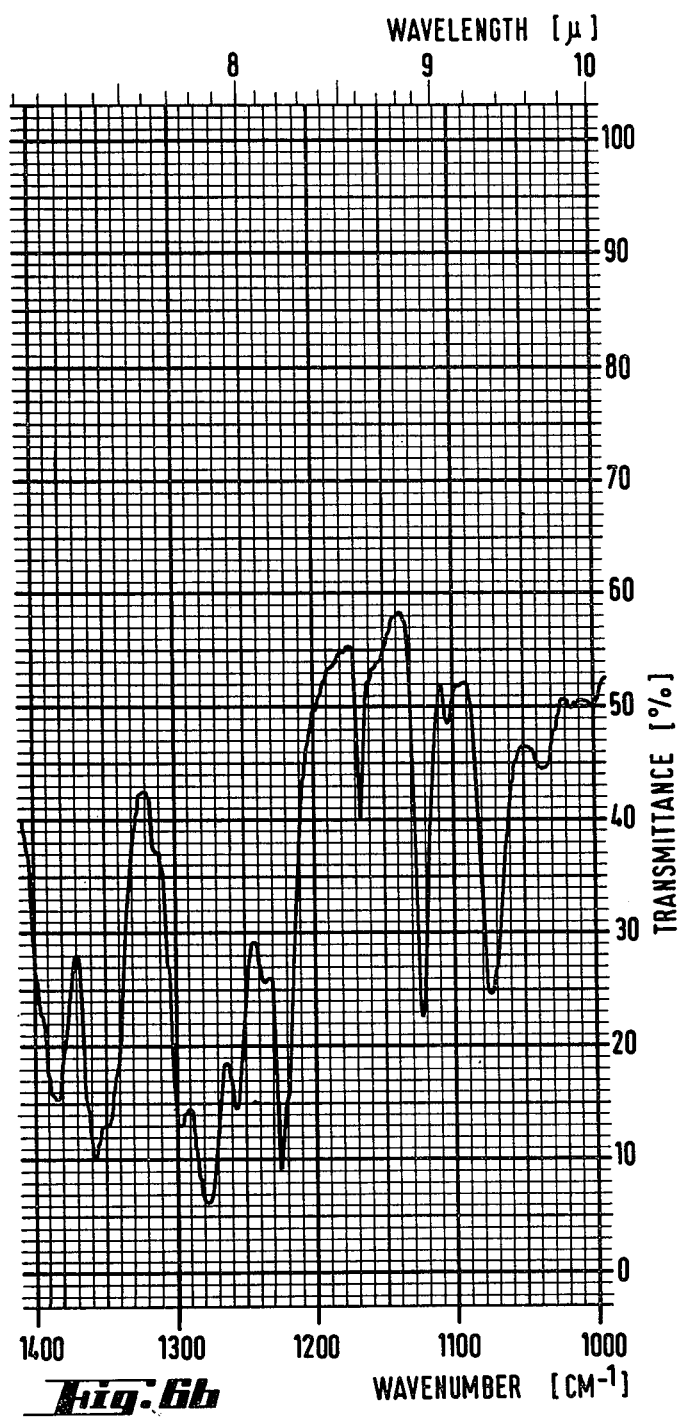

IR Spectrum KBr, see FIGS. 6a (I,II) and 6b.

The entire disclosure of German priority application No. P 3034638.4 is hereby incorporated by reference.

What is claimed is:

1. 2-amino-3-carbethoxyamino-6-(p-fluoro-benzylamino)-pyridine-maleate of the formula

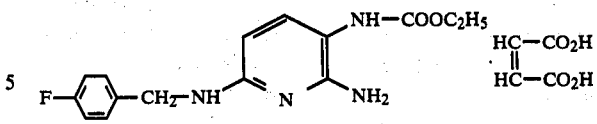

2. 2-amino-3-carbethoxyamino-6-(P-fluoro-benzylamino)-pyridine-maleate according to claim 1 consisting of 60 to 100% of crystal modification A and 40 to 0% of crystal modification B.

3. A maleate according to claim 2 containing 60 to 90% of crystal modification A.

4. A maleate according to claim 3 containing 65 to 85% of crystal modification A.

5. A maleate according to claim 4 containing 75 to 85% of crystal modification A.

6. A maleate according to claim 5 containing 78 to 82% of crystal modification A.

7. A maleate according to claim 1 having an IR spectrum, the IR spectrum being that of FIG. 2a (I, II) and 2b.

8. A maleate according to claim 1 having an IR spectrum, the IR spectrum being that of FIG. 3a (I, II) and 3b.

9. A maleate according to claim 1 having an IR spectrum, the IR spectrum being that of FIG. 4a (I, II) and 4b.

10. A maleate according to claim 1 having an IR spectrum, the IR spectrum being that of FIG. 5a (I, II) and 5b.

11. A maleate according to claim 1 having an IR spectrum, the IR spectrum being that of FIG. 6a (I, II) and 6b.

12. A process for the production of 2-amino-3-carbethoxyamino-6-(p-fluoro-benzylamino)-pyridine-maleate of the formula

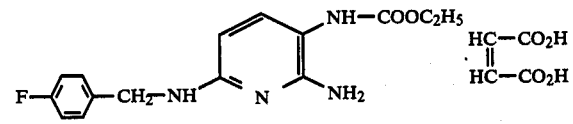

comprising reacting 1 mole of 2-amino-3-carbethoxyamino-6-(p-fluoro-benzylamino)-pyridine in a solvent with 1.1 to 1.5 moles of maleic acid between 20° C. and the boiling point of the solvent.

13. A process according to claim 12 wherein the temperature is between 20° and 60° C.

14. A process according to claim 12 wherein there is employed to form the maleate crude 2-amino-3-carbethoxyamino-6-(p-fluoro-benzylamino)-pyridine which has been treated with activated carbon to purify it and the crude pyridine employed has a melting point of 117°-120° C.

15. A process according to claim 13 wherein the maleate is crystallized out and then heated in the presence of the solvent to a temperature between 30° C. and the boiling point of the solvent for 5 to 180 minutes.

16. A process according to claim 15 wherein there is employed to form the maleate crude 2-amino-3-carbethoxyamino-6-(p-fluoro-benzylamino)-pyridine which has been treated with activated carbon to purify it and the crude pyridine employed has a melting point of 117°-120° C.

17. A process according to claim 16 which the reaction between the 2-amino-3-carbethoxyamino-6-(p-fluoro-benzylamino)-pyridine and maleic acid is carried out at a temperature between 20° and 60° C. in the presence of undissolved inoculant crystals.

18. A process according to claim 15 which the reaction between the 2-amino-3-carbethoxyamino-6-(p-fluoro-benzylamino)-pyridine and maleic acid is carried out at a temperature between 20° and 60° C. in the presence of undissolved inoculant crystals.

19. A method of treating a patient requiring an antiphlogestic agent or an analgesic agent comprising administering an effective amount of the compound of claim 1.

20. A process of treating a patient requiring an antiphlogestic agent or an analgesic agent comprising administering an effective amount of the compound of claim 2.

21. A medicinal composition suitable for use as an antiphlogestic agent or an analgesic agent, comprising an effective amount for such purpose of the 2-amino-3-carbethoxyamino-6-(p-fluoro-benzylamino)-pyridine-maleate of claim 1 and a pharmaceutically acceptable carrier.

22. A medicinal composition suitable for use as an antiphlogestic agent or an analgesic agent, comprising an effective amount for such purpose of the 2-amino-3-carbethoxyamino-6-(p-fluoro-benzylamino)-pyridine-maleate of claim 2 and a pharmaceutically acceptable carrier.

* * * * *